US011112385B2

(12) United States Patent
Lin

(10) Patent No.: US 11,112,385 B2
(45) Date of Patent: Sep. 7, 2021

(54) WATERPROOF ULTRASOUND SCANNER

(71) Applicants: Inventec (Pudong) Technology Corporation, Shanghai (CN); INVENTEC CORPORATION, Taipei (TW)

(72) Inventor: Yi-Chou Lin, Taipei (TW)

(73) Assignees: Inventec (Pudong) Technology Corporation, Shanghai (CN); INVENTEC CORPORATION, Taipei (TW)

( * ) Notice: Subject to any disclaimer, the term of this patent is extended or adjusted under 35 U.S.C. 154(b) by 423 days.

(21) Appl. No.: 16/221,571

(22) Filed: Dec. 16, 2018

(65) Prior Publication Data

US 2020/0166481 A1 May 28, 2020

(30) Foreign Application Priority Data

Nov. 26, 2018 (CN) .......................... 201811418391.3

(51) Int. Cl.
*G01N 29/24* (2006.01)
*A61B 8/00* (2006.01)
*G01N 29/22* (2006.01)

(52) U.S. Cl.
CPC ........... *G01N 29/24* (2013.01); *A61B 8/4427* (2013.01); *A61B 8/4444* (2013.01); *G01N 29/226* (2013.01); *A61B 8/4422* (2013.01); *A61B 2562/18* (2013.01); *G01N 29/22* (2013.01)

(58) Field of Classification Search
CPC ...... G01N 29/24; G01N 29/226; G01N 29/22; A61B 8/4427; A61B 8/4444; A61B 8/4422; A61B 2562/18
See application file for complete search history.

(56) References Cited

U.S. PATENT DOCUMENTS

| 7,941,196 B2* | 5/2011 | Kawasaki | H04M 1/18 455/575.8 |
| 2004/0111029 A1* | 6/2004 | Bates | A61B 8/4281 600/437 |
| 2008/0194961 A1* | 8/2008 | Randall | A61B 8/00 600/459 |
| 2010/0292575 A1* | 11/2010 | Sharp | A61B 8/4438 600/459 |
| 2013/0253327 A1* | 9/2013 | Ko | A61B 8/4411 600/459 |
| 2015/0216051 A1* | 7/2015 | Shah | H05K 3/14 174/262 |

* cited by examiner

*Primary Examiner* — Sean D Mattson
(74) *Attorney, Agent, or Firm* — CKC & Partners Co., LLC

(57) ABSTRACT

A waterproof ultrasound scanner includes a main casing, an ultrasound probe, a probe inner frame, a probe outer cover, a first waterproof member, and a second waterproof member. A circuit board is disposed inside the main casing. The ultrasound probe has at least one electric route connected to the circuit board. The probe inner frame abuts against the ultrasound probe. The probe inner frame has at least one route outlet for the electric route to pass through. The probe outer cover encloses the ultrasound probe and the inner frame, and is partially located inside the main casing. The outer cover has a first opening through which the ultrasound probe is exposed. The first waterproof member is hermetically clamped between the ultrasound probe and the inner frame. The second waterproof member is hermetically clamped between the outer cover, the inner frame, and the main casing.

9 Claims, 5 Drawing Sheets

WATERPROOF ULTRASOUND SCANNER

RELATED APPLICATIONS

This application claims priority to China Application Serial Number 201811418391.3, filed Nov. 26, 2018, the disclosure of which is incorporated herein by reference in its entirety.

BACKGROUND

Technical Field

The present disclosure relates to a waterproof ultrasound scanner.

Description of Related Art

In conventional ultrasound scanners, prevention of liquid penetration by means of interference fit between the casing and a rubber attached to the ultrasound probe is a common waterproof technique. However, ultrasound scanners adopting the technique described above have limited waterproof capability. In addition, the aforementioned technique can only provide waterproof function for the probe, not for the main body of the ultrasound scanner. The issues mentioned above render existing ultrasound scanners unusable outdoors under a bad weather condition.

Consequently, how to provide a waterproof ultrasound scanner to resolve the aforementioned issues is one of the directions that should be urgently endeavored.

SUMMARY

In view of the foregoing, one of the objects of the present disclosure is to provide an ultrasound scanner with excellent waterproof capability.

To achieve the objective stated above, in accordance with an embodiment of the present disclosure, a waterproof ultrasound scanner includes a main casing, an ultrasound probe, a probe inner frame, a probe outer cover, a first waterproof member, and a second waterproof member. A circuit board is disposed inside the main casing. The ultrasound probe has at least one electric route connected to the circuit board. The probe inner frame abuts against the ultrasound probe. The probe inner frame has at least one route outlet for the electric route to pass through. The probe outer cover encloses the ultrasound probe and the inner frame, and is partially located inside the main casing. The outer cover has a first opening through which the ultrasound probe is exposed. The first waterproof member is hermetically clamped between the ultrasound probe and the inner frame. The second waterproof member is hermetically clamped between the outer cover, the inner frame, and the main casing.

In one of more embodiments of the present disclosure, an inner edge of the first opening hermetically abuts against the ultrasound probe.

In one of more embodiments of the present disclosure, the main casing has a stopping structure located on an inner side of the main casing. The second waterproof member hermetically abuts against the stopping structure.

In one of more embodiments of the present disclosure, the main casing further has a protrusion. The stopping structure and the protrusion are located on two opposite sides of the second waterproof member. The outer cover further has a slot configured to engage with the protrusion.

In one of more embodiments of the present disclosure, the outer cover further has a second opening and a circular end surface surrounding the second opening. The second waterproof member is hermetically clamped between the circular end surface and the stopping structure.

In one of more embodiments of the present disclosure, the second waterproof member has an outer ring structure hermetically abutting against a side of the outer cover facing the main casing.

In one of more embodiments of the present disclosure, the inner frame has a recess located on a side of the inner frame away from the ultrasound probe. The second waterproof member has an inner ring structure extending into the recess and hermetically abutting against a side wall of the recess.

In one of more embodiments of the present disclosure, the first waterproof member surrounds the route outlet.

In one of more embodiments of the present disclosure, the main casing includes a first half casing and a second half casing. The waterproof ultrasound scanner further includes a third waterproof member hermetically clamped between the first half casing and the second half casing.

In one of more embodiments of the present disclosure, the first half casing and the second half casing each has an outer edge. The second half casing further has a depressed structure disposed along the outer edge of the second half casing. The third waterproof member is hermetically clamped between the outer edge of the first half casing and the depressed structure.

In sum, the waterproof ultrasound probe incorporates multiple waterproof members (including waterproof gaskets and waterproof strips) to form watertight seals along possible liquid-penetrating paths, thereby resolving the problem of having poor waterproof capability of conventional ultrasound scanners.

BRIEF DESCRIPTION OF THE DRAWINGS

To make the objectives, features, advantages, and examples of the present invention, including those mentioned above and others, more comprehensible, descriptions of the accompanying drawings are provided as follows.

DETAILED DESCRIPTION

Figure 1:
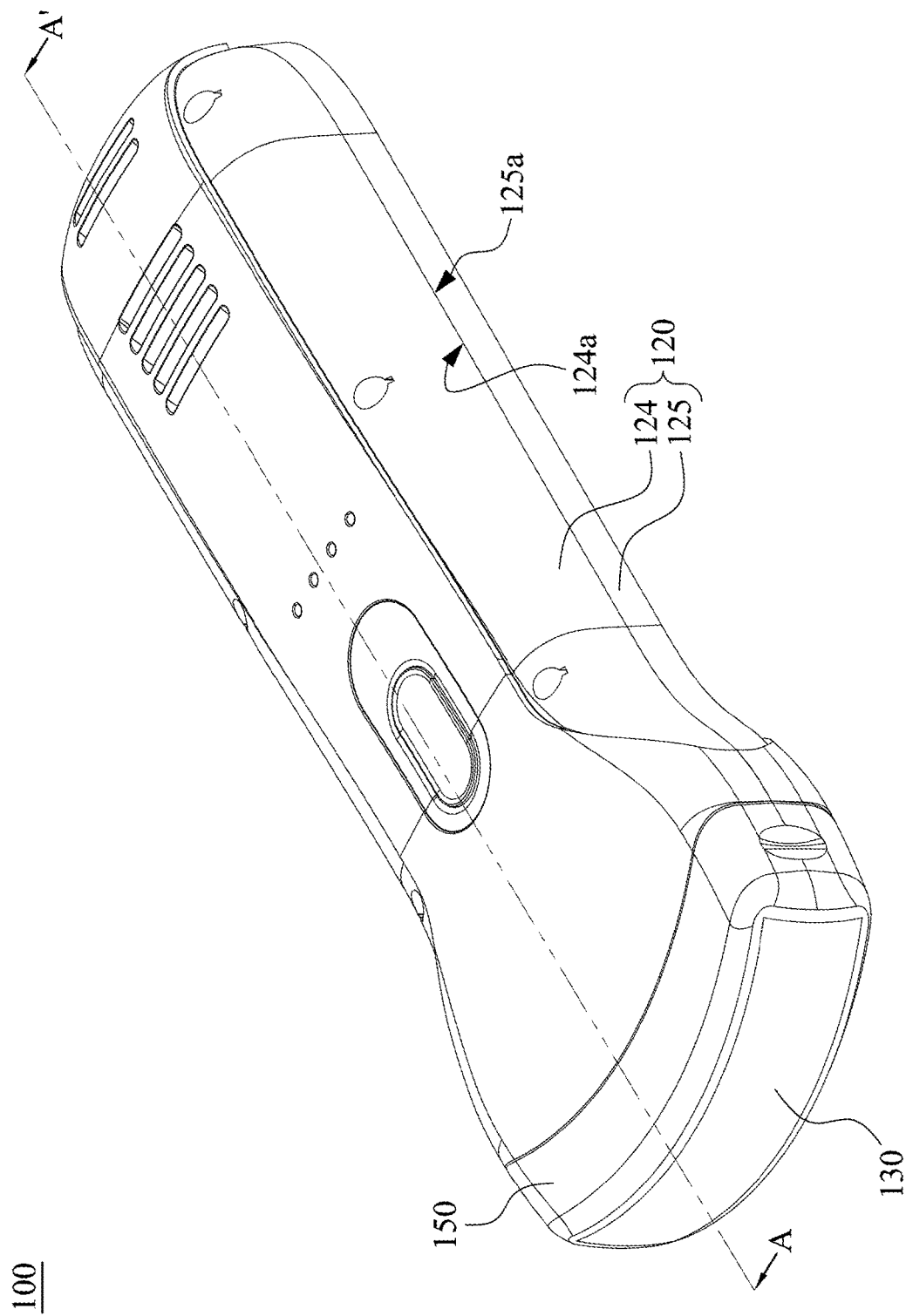
FIG. 1 illustrates an assembled view of a waterproof ultrasound scanner in accordance with an embodiment of the present disclosure.

For the sake of the completeness of the description of the present disclosure, reference is made to the accompanying drawings and the various embodiments described below. Various features in the drawings are not drawn to scale and are provided for illustration purposes only. To provide full understanding of the present disclosure, various practical details will be explained in the following descriptions. However, a person with an ordinary skill in relevant art should realize that the present disclosure can be implemented without one or more of the practical details. Therefore, these details should not be used to limit the present disclosure.

Figure 2:
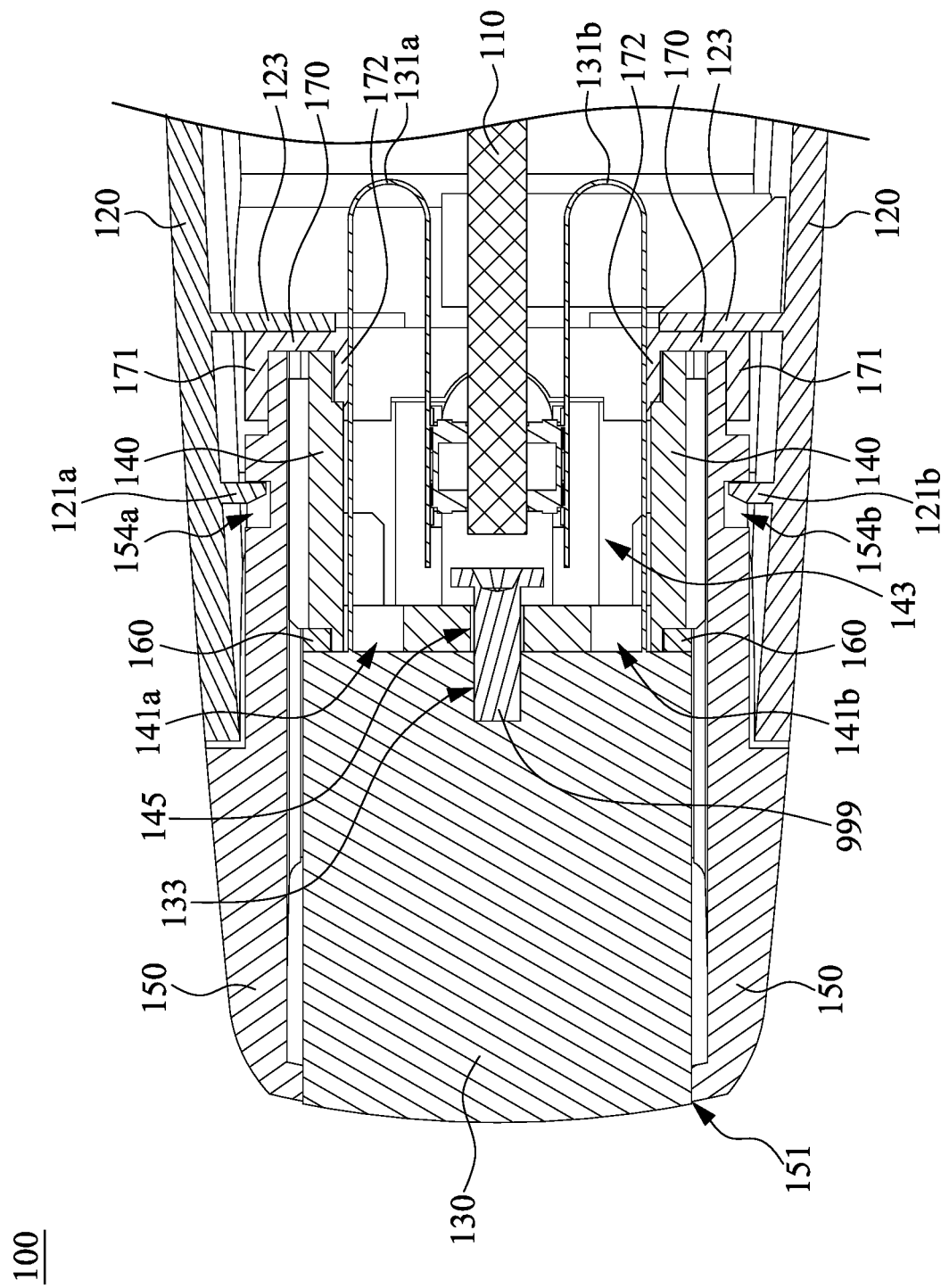
FIG. 2 is a partially enlarged cross-sectional view of the waterproof ultrasound scanner shown in FIG. 1 taken along line A-A'.

Please refer to FIG. 1 and FIG. 2. FIG. 1 illustrates an assembled view of a waterproof ultrasound scanner 100 in accordance with an embodiment of the present disclosure. FIG. 2 is a partially enlarged cross-sectional view of the waterproof ultrasound scanner 100 shown in FIG. 1 taken along line A-A'. As shown in FIG. 2, the waterproof ultrasound scanner 100 includes a control circuit board 110, a main casing 120, an ultrasound probe 130, an inner frame 140, an outer cover 150, a first waterproof member 160, and a second waterproof member 170. Functionalities and features of the aforementioned components will be discussed in detail below.

Figure 3:
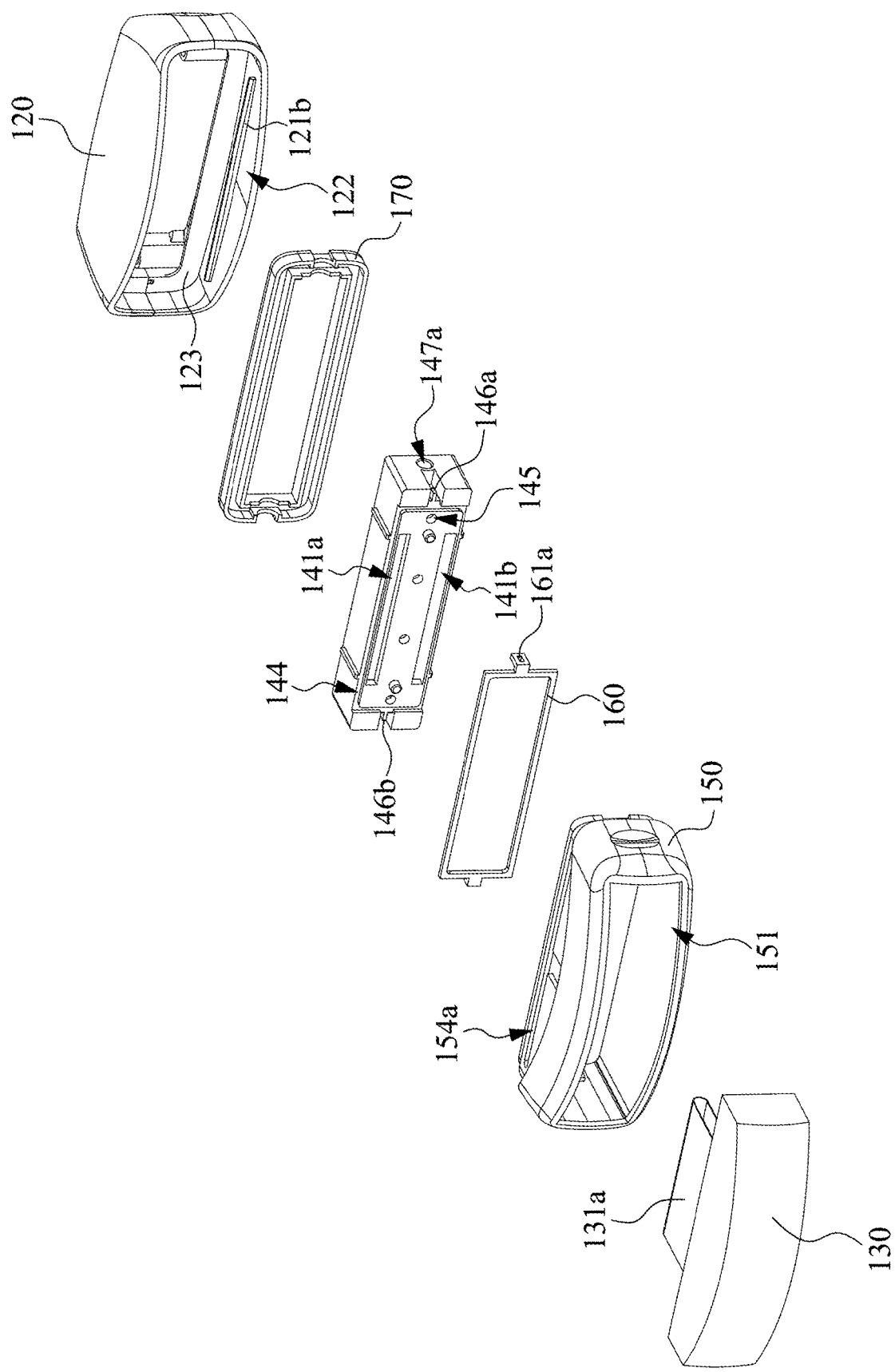
FIG. 3 is an exploded view of the waterproof ultrasound scanner shown in FIG. 1 take from a view angle.
Figure 4:
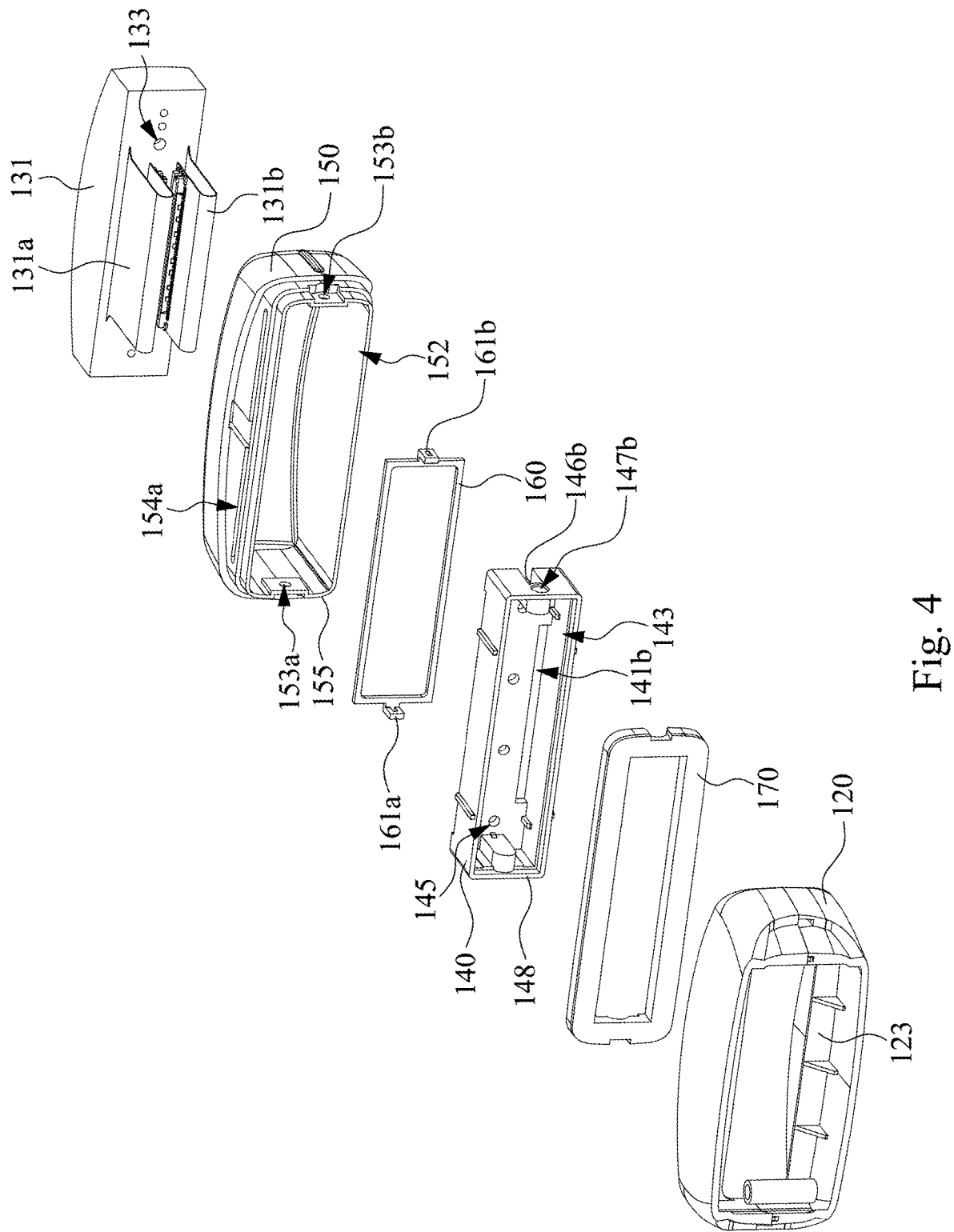
FIG. 4 is an exploded view of the waterproof ultrasound scanner shown in FIG. 1 take from another view angle.

Please also refer to FIG. 3 and FIG. 4, which are exploded views of the waterproof ultrasound scanner 100 shown in FIG. 1 take from two different view angles. It should be noted that, in order to clearly convey the main technical features of the present disclosure, only a portion of the main casing 120 adjacent to the outer cover 150 is illustrated in FIG. 3 and FIG. 4, and the control circuit board 110 is omitted in FIG. 3 and FIG. 4. As shown in FIG. 2, the control circuit board 110 is disposed inside the main casing 120. The outer cover 150 is fixed to the main casing 120 and partially located inside the main casing 120. The main casing 120 has a front opening 122, and the outer cover 150 is partially inserted into the main casing 120 through the front opening 122. The outer cover 150 is a hollow structure with two open ends. The outer cover 150 has a first opening 151 (as shown in FIG. 3) on its front side, and a second opening 152 (as shown in FIG. 4) on its rear side. The outer cover 150 encloses the ultrasound probe 130 and the inner frame 140 to protect the ultrasound probe 130 and the inner frame 140.

As shown in FIG. 2, the ultrasound probe 130 is exposed through the first opening 151 of the outer cover 150, so as to emit a sound wave towards a test object and record a reflected wave. In some embodiments, an inner edge of the first opening 151 hermetically abuts against the ultrasound probe 130, thereby preventing liquid from penetrating through a gap between the ultrasound probe 130 and the outer cover 150. For example, an outer surface of the ultrasound probe 130 is made of rubber. Before the ultrasound probe 130 and the outer cover 150 are assembled, a cross-sectional area of the first opening 151 is smaller than a cross-sectional area of the ultrasound probe 130. Therefore, the assembler must apply force to insert the ultrasound probe 130 into the first opening 151, so that the ultrasound probe 130 and the outer cover 150 can be fitted together. After the ultrasound probe 130 and the outer cover 150 are assembled, the aforementioned dimensional difference results in an interference fit between the ultrasound probe 130 and the outer cover 150, through which the waterproof function is achieved.

As shown in FIG. 2, the inner frame 140 abuts against a side of the ultrasound probe 130 away from the first opening 151. The ultrasound probe 130 has two electric routes 131a, 131b (also refer to FIG. 4), and the inner frame 140 has two route outlets 141a, 141b (also refer to FIG. 3). The electric routes 131a, 131b passes through the route outlets 141a, 141b respectively, and electrically couples the control circuit board 110. In the present embodiment, electric routes 131a, 131b are flexible printed circuits, and the route outlets 141a, 141b have narrow shapes corresponding to the flexible printed circuits.

In some embodiments, as shown in FIG. 2, the inner frame 140 has a recess 143 located on a side of the inner frame 140 away from the ultrasound probe 130. The route outlets 141a, 141b are positioned at the bottom of the recess 143. The control circuit board 110 extends into the recess 143 through the second opening 152 of the outer cover 150 and electrically couples the electric routes 131a, 131b passing through the route outlets 141a, 141b respectively.

Despite the fact that the electric routes 131a, 131b pass through the second opening 152 of the outer frame 150 and are folded back into the recess 143 of the inner frame 140 to electrically couple the control circuit board 110, the present disclosure is not limited thereto. In some embodiments, the electric routes 131a, 131b are provided with shorter lengths such that they do not pass through the second opening 152 of the outer frame 150 and are not folded back. In some embodiments, the control circuit board 110 does not extend into the recess 143 of the inner frame 140. The electric routes 131a, 131b extend into the main casing 120 through the second opening 152 of the outer frame 150 to electrically couple the control circuit board 150.

As shown in FIG. 2, the first waterproof member 160 is a waterproof gasket having a closed ring shape. The first waterproof member 160 is hermetically clamped between the ultrasound probe 130 and the inner frame 140. Specifically, the inner frame 140 has a depressed portion 144 (also refer to FIG. 3) surrounding the route outlets 141a, 141b and facing the ultrasound probe 130. A portion of the inner frame 140 enclosed by the depressed portion 144 directly abuts against the ultrasound probe 130, and the first waterproof member 160 is clamped between the depressed portion 144 and the ultrasound probe 130. With the aforementioned structural configuration, the first waterproof member 160 surrounds and seals the route outlets 141a, 141b, thereby preventing liquid from penetrating through a gap between the ultrasound probe 130 and the inner frame 140 and contacting the electric routes 131a, 131b, or further flowing through the route outlets 141a, 141b and contacting the control circuit board 110.

In some embodiments, as shown in FIG. 2, the inner frame 140 has a plurality of first securing holes 145 (also refer to FIG. 4), and the ultrasound probe 130 has a plurality of second securing holes 133 (also refer to FIG. 4) positioned corresponding to the first securing holes 145. A plurality of securing members 999 (e.g., screws) each passes through a corresponding first securing hole 145 and a corresponding second securing hole 133 in sequence to hold the ultrasound probe 130 and the inner frame 140 tightly together. Consequently, the first waterproof member 160 is firmly clamped between the ultrasound probe 130 and the inner frame 140 and thus does not easily fall off. As a result, the waterproof ultrasound scanner 100 may maintain its excellent waterproof capability.

In some embodiments, before the waterproof ultrasound scanner 100 is assembled, a thickness of the first waterproof member 160 is slightly greater than a depth of the depressed portion 144. After the ultrasound scanner 100 is assembled, the aforementioned dimensional difference results in the first waterproof member 160 being slightly compressed and remaining tightly fitted with the inner frame 140 and the ultrasound probe 130, thereby achieving excellent waterproof capability.

In some embodiments, as shown in FIG. 3 and FIG. 4, the first waterproof member 160 has two first engaging portions 161a, 161b extending from both sides thereof. Correspondingly, the inner frame 140 has two second engaging portions 146a, 146b located on both sides thereof. The first engaging portions 161a, 161b are configured to engage with the second engaging portions 146a, 146b such that the first waterproof member 160 is maintained in a state of hermetically abutting against the inner frame 140.

In some embodiments, as shown in FIG. 3 and FIG. 4, the outer cover 150 has two third securing holes 153a, 153b located on both sides thereof. Correspondingly, the inner frame 140 has two fourth securing holes 147a, 147b located on both side thereof. The third securing holes 153a, 153b and the fourth securing holes 147a, 147b are configured to allow two fixing members (such as two screws, not shown) to pass through, so as to hold the inner frame 140 and the outer cover 150 together.

Although the outer cover 150 and the ultrasound probe 130 and the inner frame 140 therein can block the front opening 122 of the main casing 120, the aforementioned components cannot hermetically seal the front opening 122, as liquid may still be able to penetrate through a gap between the main casing 120 and the outer cover 150. The second waterproof member 170 is incorporated to cope with the issue describe above. As shown in FIG. 2, the second waterproof member 170 is a waterproof gasket having a closed ring shape. The second waterproof member 170 is hermetically clamped between the outer cover 150, the inner frame 140, and the main casing 120, so as to form a watertight seal in the gap between the main casing 120 and the outer cover 150.

Specifically, as shown in FIG. 2, the outer cover 150 has a first circular end surface 155 surrounding the second opening 152. The inner frame 140 has a second circular end surface 148 surrounding the recess 143. The first circular end surface 155 is coplanar with the second circular end surface 148, and both hermetically abut against the left side of the second waterproof member 170. The main casing 150 has a stopping structure 123. The stopping structure 123 is a circular wall (as shown in FIG. 3) located on the inner side of the main casing 120 and hermetically abutting against the right side of the second waterproof member 170. In other words, the second waterproof member 170 is hermetically clamped between the first circular end surface 155 of the outer cover 150, the second circular end surface 148 of the inner frame 140, and the stopping structure 123 of the main casing 120, so as to protect the electric routes 131a, 131b and the control circuit board 110 located inside the main casing 120 and the recess 143.

In some embodiments, as shown in FIG. 2, the main casing 120 has two protrusions 121a, 121b (also refer to FIG. 3). The protrusions 121a, 121b project from an inner surface of the main casing 120 and extend towards each other. The outer cover 150 has two slots 154a, 154b (also refer to FIG. 3) configured to engage with the protrusions 121a, 121b respectively. The stopping structure 123 and the protrusions 121a, 121b are located on two opposite sides of the second waterproof member 170. When the protrusions 121a, 121b engage with the slots 154a, 154b, the stopping structure 123 of the main casing 120 pushes the second waterproof member 170 rightward. Consequently, the second waterproof member 170 is firmly clamped between the outer cover 150, the inner frame 140, and the main casing 120, and thus does not easily fall off. As a result, the waterproof ultrasound scanner 100 may maintain its excellent waterproof capability.

In some embodiments, as shown in FIG. 2, the second waterproof member 170 has an outer ring structure 171. The outer ring structure 171 is a circular protruding structure (as shown in FIG. 3). The outer ring structure 171 extends towards the protrusions 121a, 121b and hermetically abuts against a side of the outer cover 150 facing the main casing 120. Therefore, liquid penetrating through the gap between the main casing 120 and the outer cover 150 may be blocked more effectively.

In some embodiments, as shown in FIG. 2, the second waterproof member 170 further has an inner ring structure 172. The inner ring structure 172 is a circular protruding structure (as shown in FIG. 3). The inner ring structure 172 extends into the recess 143 of the inner frame 140 and hermetically abuts against a side wall of the recess 143. The incorporation of the inner ring structure 172 may further enhance the waterproof capability of the second waterproof member 170. With the outer ring structure 171 and the inner ring structure 172, the second waterproof member 170 tightly wraps the first circular end surface 155 of the outer cover 150 and the second circular end surface 148 of the inner frame 140, thereby forming a watertight seal in the gap between the main casing 120 and the outer cover 150.

Figure 5:
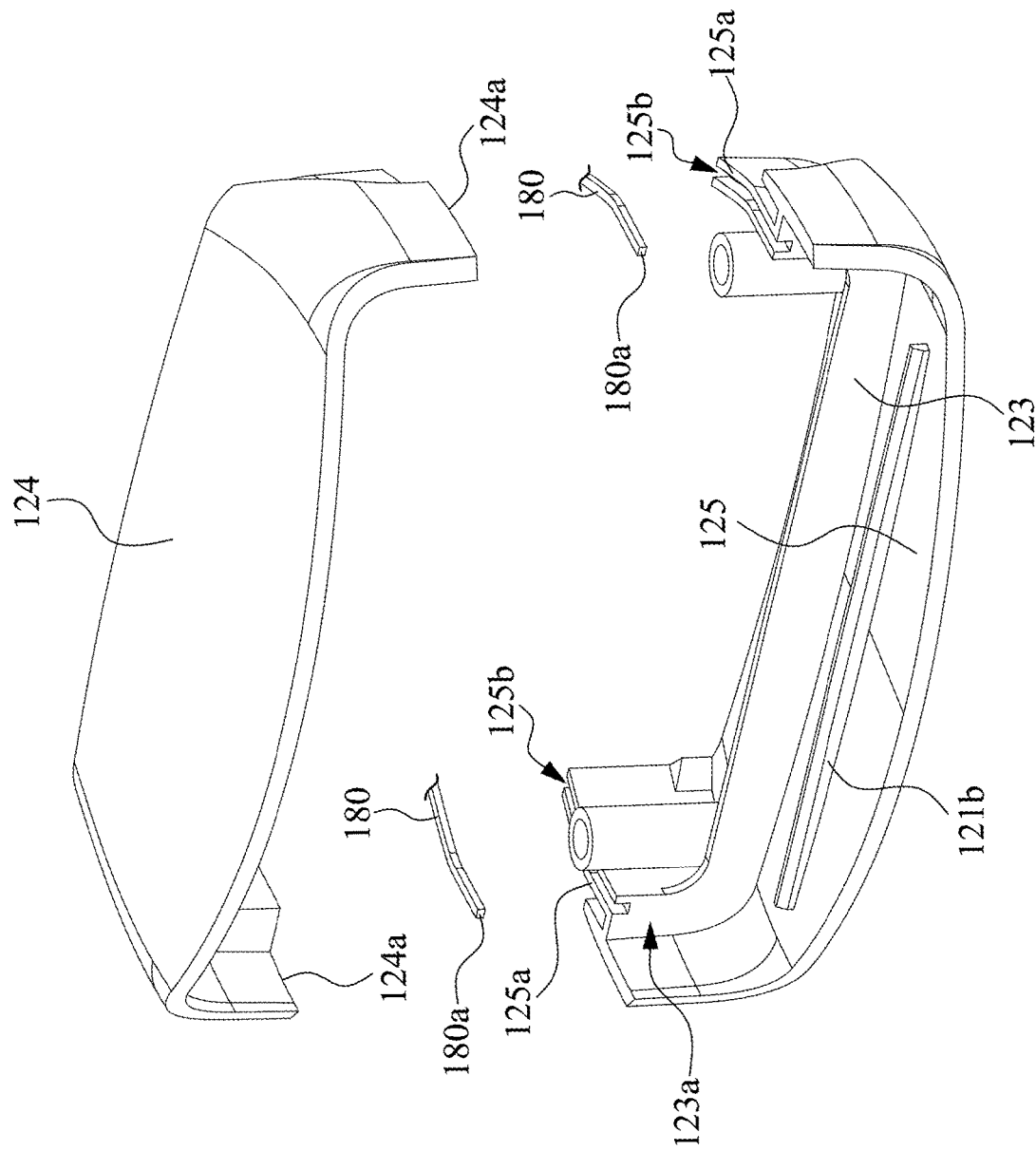
FIG. 5 is an exploded view of some components of the waterproof ultrasound scanner shown in FIG. 1.

Please refer to FIG. 5, which is an exploded view of some components of the waterproof ultrasound scanner 100 shown in FIG. 1. In some embodiments, the main casing 120 includes a first half casing 124 and a second half casing 125. To prevent liquid from penetrating through a gap between the first half casing 124 and the second half casing 125, the waterproof ultrasound scanner 100 further includes a third waterproof member 180. The third waterproof member 180 is hermetically clamped between the first half casing 124 and the second half casing 125 to form a watertight seal.

Specifically, the first half casing 124 and the second half casing 125 each has a U-shaped outer edge (i.e., outer edge 124a of the first half casing 124 and outer edge 125a of the second half casing 125, as shown in FIG. 1). The second half casing 125 further has a depressed structure 125b disposed along the outer edge 125a of the second half casing 125 and communicating with a surface 123a of the stopping structure 123 facing the second waterproof member 170. The third waterproof member 180 is a substantially U-shaped waterproof strip (only a tail portion of the third waterproof member 180 is illustrated in FIG. 5) extending along the outer edges 124a, 125a. The third waterproof member 180 is hermetically clamped between the outer edge 124a of the first half casing 124 and the depressed structure 125b of the second half casing 125, and the two ends of the third waterproof member 180 hermetically abut against the second waterproof member 170 (referring to FIG. 3). Therefore, the third waterproof member 180 can effectively form a watertight seal in the gap between the first half casing 124 and the second half casing 125.

In sum, the waterproof ultrasound probe incorporates multiple waterproof members (including waterproof gaskets and waterproof strips) to form watertight seals along possible liquid-penetrating paths, thereby resolving the problem of having poor waterproof capability of conventional ultrasound scanners.

Although the present disclosure has been disclosed by the above embodiments, the present disclosure is not limited thereto. Any person skilled in the art can make various changes and modifications without departing from the spirit and the scope of the present disclosure. Therefore, the protective scope of the present disclosure shall be the scope of the claims as attached.

What is claimed is:
1. A waterproof ultrasound scanner, comprising:
a main casing inside which a circuit board is disposed;
an ultrasound probe having at least one electric route connected to the circuit board;

an inner frame abutting against the ultrasound probe and having at least one route outlet for the at least one electric route to pass through;

an outer cover enclosing the ultrasound probe and the inner frame, wherein the outer cover is partially located inside the main casing and has a first opening through which the ultrasound probe is exposed;

a first waterproof member hermetically clamped between the ultrasound probe and the inner frame; and a second waterproof member hermetically clamped between the outer cover, the inner frame, and the main casing, wherein the inner frame has a recess located on a side of the inner frame away from the ultrasound probe, and the second waterproof member has an inner ring structure extending into the recess and hermetically abutting against a side wall of the recess.

2. The waterproof ultrasound scanner of claim 1, wherein an inner edge of the first opening hermetically abuts against the ultrasound probe.

3. The waterproof ultrasound scanner of claim 1, wherein the main casing has a stopping structure located on an inner side of the main casing, and the second waterproof member hermetically abuts against the stopping structure.

4. The waterproof ultrasound scanner of claim 3, wherein the main casing further has a protrusion, the stopping structure and the protrusion are located on two opposite sides of the second waterproof member, the outer cover further has a slot configured to engage with the protrusion.

5. The waterproof ultrasound scanner of claim 3, wherein the outer cover further has a second opening and a circular end surface surrounding the second opening, the second waterproof member is hermetically clamped between the circular end surface and the stopping structure.

6. The waterproof ultrasound scanner of claim 1, wherein the second waterproof member has an outer ring structure hermetically abutting against a side of the outer cover facing the main casing.

7. The waterproof ultrasound scanner of claim 1, wherein the first waterproof member surrounds the at least one route outlet.

8. The waterproof ultrasound scanner of claim 1, wherein the main casing comprises:

a first half casing; and a second half casing, wherein the waterproof ultrasound scanner further comprises a third waterproof member hermetically clamped between the first half casing and the second half casing.

9. The waterproof ultrasound scanner of claim 8, wherein the first half casing and the second half casing each has an outer edge, the second half casing further has a depressed structure disposed along the outer edge of the second half casing, the third waterproof member is hermetically clamped between the outer edge of the first half casing and the depressed structure.

* * * * *